(12) United States Patent
Hasegawa

(10) Patent No.: US 6,710,882 B2
(45) Date of Patent: Mar. 23, 2004

(54) ANISOTROPY ANALYZING METHOD AND AN ANISOTROPY ANALYZING APPARATUS

(75) Inventor: Tomiichi Hasegawa, Niigata Pref. (JP)

(73) Assignee: Niigata University, Niigata Pref. (JP)

( * ) Notice: Subject to any disclaimer, the term of this patent is extended or adjusted under 35 U.S.C. 154(b) by 95 days.

(21) Appl. No.: 09/903,999

(22) Filed: Jul. 12, 2001

(65) Prior Publication Data
US 2002/0048024 A1 Apr. 25, 2002

(30) Foreign Application Priority Data
Oct. 24, 2000 (JP) ........................... 2000-323520

(51) Int. Cl.⁷ ................................. G01B 9/02
(52) U.S. Cl. ...................................... 356/491
(58) Field of Search ................ 356/491, 492, 356/493, 495, 73.1

(56) References Cited

U.S. PATENT DOCUMENTS

| | | |
|---|---|---|
| 4,671,660 A | 6/1987 | Distl et al. |
| 4,822,169 A | 4/1989 | Distl et al. |
| 4,914,487 A | 4/1990 | Croizer et al. |
| 5,517,022 A | 5/1996 | Bock et al. |
| 5,604,591 A * | 2/1997 | Kitagawa ............... 356/491 |
| 5,694,217 A | 12/1997 | Hizuka |
| 5,706,084 A * | 1/1998 | Gutierrez ............... 356/517 |
| 5,712,704 A * | 1/1998 | Martin et al. .......... 356/491 |
| 5,949,546 A * | 9/1999 | Lee et al. ............... 356/492 |
| 6,341,015 B2 * | 1/2002 | Shirley .................. 356/517 |

FOREIGN PATENT DOCUMENTS

| | | | |
|---|---|---|---|
| EP | 0 209 721 A | 1/1987 | |
| EP | 0 209 721 A1 * | 1/1987 | ............ G01D/5/26 |
| EP | 0 319 923 A | 6/1989 | |
| EP | 0 338 288 A2 | 10/1989 | |
| EP | 0 933 629 A | 8/1999 | |
| GB | 2 307 965 A | 6/1997 | |
| JP | 8-15155 | 1/1996 | |
| JP | 10-622568 | 3/1998 | |
| RU | 1640542 | 7/1991 | |
| RU | 2 102 700 C | 1/1998 | |
| SU | 1 640 542 A | 7/1991 | |

OTHER PUBLICATIONS

Photoelastic Testing Using a Birefringence–Sensitive Interferometer, Kallol Bhattacharya et al., Optics Communications, North–Holland Publishing Co., Amsterdam, NL., vol. 109, No. 5/6, Jul. 15, 1994, pp. 380–386, XP000454741.

Visualisation of Dynamic Flow Birefringence of Cardiovascular Models, Sun Y–D et al., Optics and Laser Technology, Elsevier Science Publishers BV., Amsterdam, NL, vol. 31, No. 1, Feb. 1999, pp. 103–112, XP004173574.

Bhattacharya, K.: "*Photoelastic testing using a birefringence–sensitive interferometer*", Optics Communications 109 (1994) 380–386.

* cited by examiner

*Primary Examiner*—David V. Bruce
*Assistant Examiner*—Thomas R Artman
(74) *Attorney, Agent, or Firm*—Knobbe Martens Olson & Bear, LLP

(57) ABSTRACT

A light beam from a laser source is divided into two light beams at a half mirror, and the plane of polarization of one of the two divided light beams is rotated by 90 degrees at a half-wave plate so as to be orthogonal to that of the other of the two divided light beams. The two divided light beams are superimposed and introduced into a sample to be measured in anisotropy. After passing through the sample, the superimposed light beam is split at a polarized light beam splitter into the above two light beams, and the plane of polarization of the other of the two light beam is rotated by 90 degrees at a half-wave plate so as to correspond to that of the one of the two light beams. Then, the two light beams is superimposed again at a half mirror, and an interference pattern of the superimposed light beam is projected on a screen.

14 Claims, 2 Drawing Sheets

ANISOTROPY ANALYZING METHOD AND AN ANISOTROPY ANALYZING APPARATUS

BACKGROUND OF THE INVENTION

1. Field of the Invention

This invention relates to a method for analyzing the anisotropy of a given substance and an apparatus for analyzing the anisotropy of the given substance which take advantage of optical interference, particularly to an anisotropy analyzing method and an anisotropy analyzing apparatus preferably usable for the anisotropy observation in a stress condition of a viscoelastic fluid.

2. Description of the Prior Art

Conventionally, for measuring and analyzing an anisotropy such as a difference in normal stresses of a viscoelastic fluid, a light beam is modulated electrically or mechanically to generate plural light beams alternately in time of which the planes of polarization are orthogonal each other. Then, the thus obtained plural light beams are introduced into the viscoelastic fluid, and are analyzed after passing through the viscoelastic fluid. Therefore, for detecting the transmitted plural light beams as an output signal, it is required that the plural light beams are synchronized electrically before the introduction.

As a result, the measuring system becomes complicated entirely and requires expensive instruments. Moreover, the above anisotropy measuring method can not measure the anisotropy in a given area at the same time.

SUMMARY OF THE INVENTION

It is an object of the present invention to provide a new anisotropy analyzing method which can measure an anisotropy of a given substance in a given area at the same time and an anisotropy analyzing apparatus to be preferably employed in the anisotropy analyzing method.

For achieving the above object, this invention relates to an anisotropy analyzing method comprising the steps of:

preparing two light beams having the same wavelength of which the plane of polarization are crossed at a given angle, introducing the two light beams into a sample to be measured in anisotropy at the same time, rotating the plane of polarization of one of the two light beams by the given angle so as to correspond to that of the other of the two light beams, after passing the two light beams through the sample, superimposing the two light beams, and observing an interference pattern of the thus obtained superimposed light beam.

That is, in the anisotropy analyzing method of the present invention, first of all, two light beam are generated continuously in time of which the planes of polarization are crossed at a given angle, which is different from the above conventional method. Then, the two light beams are introduced into a sample to be measured in anisotropy at the same time, and are superimposed after passing through the sample so that their planes of polarization corresponds each other. Then, the interference pattern of the superimposed light beam is observed.

If the sample has an anisotropy such as a stress difference, at least one of the two light beams of which the planes of polarization are crossed each other is changed in refractive index because of the anisotropy. Therefore, the interference pattern of the anisotropic sample is shifted from that of a non-anisotropic sample. Consequently, the anisotropy of the sample can be measured qualitatively by observing the interference pattern shift.

Moreover, if the parameters relating the interference pattern shift to the anisotropy of the sample are known, the anisotropy can be measured quantitatively.

As mentioned above, since in the anisotropy analyzing method of the present invention, the two light beams which are continuous in time and of which the planes of polarization are crossed at a given angle are employed, the conventional electric synchronization for the plural light beams is not required. Therefore, the measuring system can be simplified entirely, and does not require expensive instruments, so that the cost of the total measuring system can be reduced. Moreover, since the two light beams are introduced into the sample, and irradiated to a given area of the sample at the same time, the anisotropy around the given area of the sample can be measured at the same time.

Moreover, the anisotropy of the sample can be measured without the density fluctuation due to the temperature change and pressure change of the sample, and the momentary structural change can be also measured.

In a preferred embodiment of the present invention, the two light beams having their respective crossing planes of polarization are superimposed before they are introduced into the sample, and the thus obtained superimposed light beam is introduced into the sample. Thereby, the anisotropy of the sample can be measured easily over the traveling direction of the light beam, for example, over the thickness direction of the sample.

In another preferred embodiment of the present invention, the two light beams having their respective crossing planes of polarization are introduced into the sample so that their beam directions are crossed each other by a small angle. In this case, the two light beams are crossed at a given position inside the sample.

The anisotropy measuring apparatus of the present invention, for realizing the above measuring method, comprises:

before a sample to be measured in anisotropy, a laser source to generate and oscillate a light beam to be used in anisotropy analysis a light beam-dividing means to divide a light beam from the laser source into two light beams, and a first plane of polarization-rotating means to rotate the plane of polarization of one of the thus obtained two divided light beams by a given angle, after the sample to be measured in anisotropy, a second plane of polarization-rotating means to rotate the plane of polarization of the one or the other of the two divided light beams by the given angle so that their planes of polarization can correspond each other, a light beam-superimposing means to superimpose the two divided light beams, and a light beam-projecting means to project and observe an interference pattern of the thus obtained superimposed light beam.

In the case of introducing the superimposed light beam into the sample according to the above preferred embodiment of the anisotropy measuring method, the anisotropy measuring apparatus has additional light beam-superimposing means to superimpose the divided light beams after the first plane of polarization-rotating means before the sample to be analyzed in anisotropy.

A half-wave plate may be preferably employed as the plane of polarization-rotating means. Since the half-wave plate is available in low cost, the use of the half-wave plate can reduce the cost of the total apparatus. In this case, since the plane of polarization of the one divided light beam is rotated by 90 degrees, it can measure the anisotropy of the sample in the orthogonal direction with the other divided light beam.

Moreover, this invention relates to an anisotropy analyzing method comprising the steps of:

preparing a single polarized light beam, introducing the single polarized light beam into a sample to be measured, dividing the single polarized light beam into two light beams, after passing through the sample, superimposing the two divided light beams, and observing an interference pattern of the thus obtained superimposed light beam.

In the above anisotropy analyzing method of the present invention, the two light beams of which the planes of polarization are crossed at a given angle are employed to analyze the anisotropy of the sample, but in this anisotropy analyzing method of the present invention, a single plane polarized light beam, a single circularly polarized light beam or a single elliptically polarized light beam is employed.

In this case, since the single polarized light beam is divided into the two light beams after passing through the sample, and the two divided light beams are superimposed, the anisotropy of the sample can be measured from the observation of the interference pattern of the superimposed light beam.

BRIEF DESCRIPTION OF THE DRAWINGS

For better understanding of the present invention, reference is made to the attached drawings, wherein.

DESCRIPTION OF THE PREFERRED EMBODIMENTS

Figure 1:
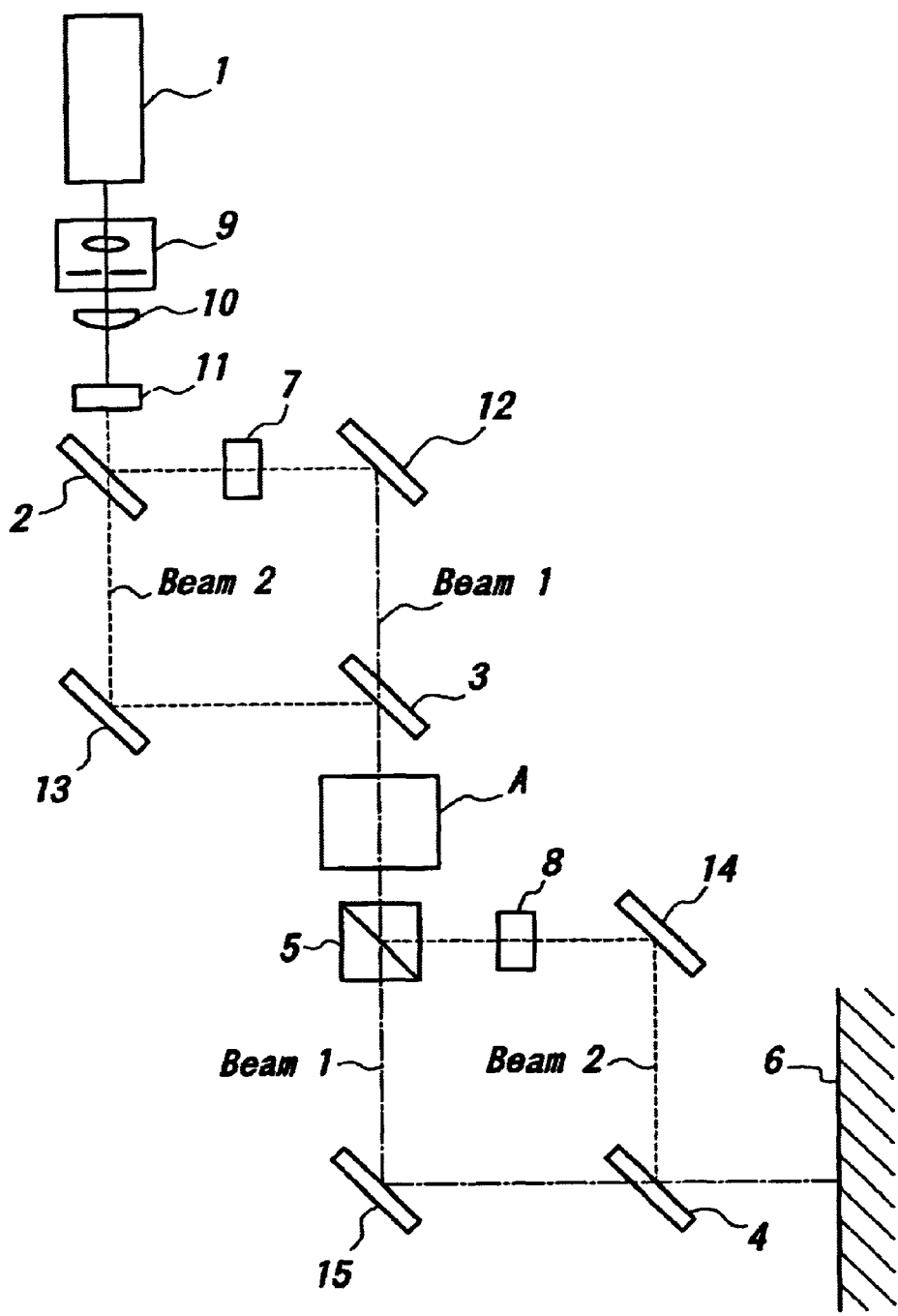
FIG. 1 is a structural view of an anisotropy analyzing apparatus according to the present invention, employed in a preferred embodiment of the anisotropy analyzing method of the present invention.

FIG. 1 is a structural view of an anisotropy analyzing apparatus according to the present invention, employed in a preferred embodiment of the anisotropy analyzing method of the present invention.

An anisotropy analyzing apparatus depicted in FIG. 1 has a laser source 1 to generate and oscillate a light beam to be used in the anisotropy analysis of a sample A, half mirrors 2, 3, 4 and a polarized light beam splitter 5 to divide the light beam from the laser source and superimpose the divided light beams, and a screen 6 to project an interference pattern to analyze an anisotropy of the sample A.

Moreover, the anisotropy analyzing apparatus has half-wave plates 7 and 8 to rotate the light beam by 90 degrees, a spacial filter 9, a collimator lens 10, a polarizing plate 11, and mirrors 12, 13, 14, 15 to reflect the light beam and change the traveling direction.

A laser light beam from the laser source 1 passes through the spacial filter 9 and the collimator lens 10, and thus, widened. Then, the light beam passes through the polarizing plate 11 to be converted into a plane wave. The plane wave is divided into two light beams through the half mirror 2.

One of the two divided light beams (beam 1) is transmitted to the half-wave plate 7, and then, its plane of polarization is rotated by 90 degrees through the half-wave plate 7. The beam 1 is reflected at the mirror 12 and transmitted to the half mirror 3. The other of the two divided light beam (beam 2) is reflected at the mirror 13 and is transmitted to the half mirror 3 through the change of the traveling direction.

At the half mirror 3, the beam 1 and beam 2 having their respective orthogonal planes of polarization through the above 90 degrees rotation are superimposed. The thus obtained superimposed light beam is introduced into the sample A. The superimposed light beam passes through the sample A, and then, is transmitted to the polarized light beam splitter 5.

At the polarized light beam splitter 5, the superimposed light beam is divided into two light beams 1 and 2 having their respective orthogonal planes of polarization. The plane of polarization of the beam 2 is rotated by 90 degrees at the half-wave plate 8 so as to correspond to that of the beam 1. Then, the beam 2 is reflected at the mirror 14 and transmitted to the half mirror 4 through the change of the traveling direction by 90 degrees. The beam 1 is reflected at the mirror 15 and transmitted to the half mirror 4 through the change of the traveling direction by 90 degrees.

The beams 1 and 2 having the same plane of polarization are superimposed at the half mirror 4, and then, an interference pattern from the superimposed light beam is projected on the screen 6.

In this case, if the sample A has, in the traveling direction of the light beam, an anisotropy such as a stress difference in the polarizing directions, the interference pattern is shifted from a normal interference pattern. Therefore, if the normal interference pattern is used as a standard interference pattern, the anisotropy of the sample A can be measured qualitatively from the degree of the interference pattern shift.

Moreover, if the parameters relating the interference pattern shift to the anisotropy of the sample A are known, the anisotropy can be measured quantitatively.

Furthermore, since the superimposed light beam is introduced into the sample A in the thickness direction as shown in FIG. 1, the anisotropy of the sample A can be measured over the thickness direction.

Figure 2:
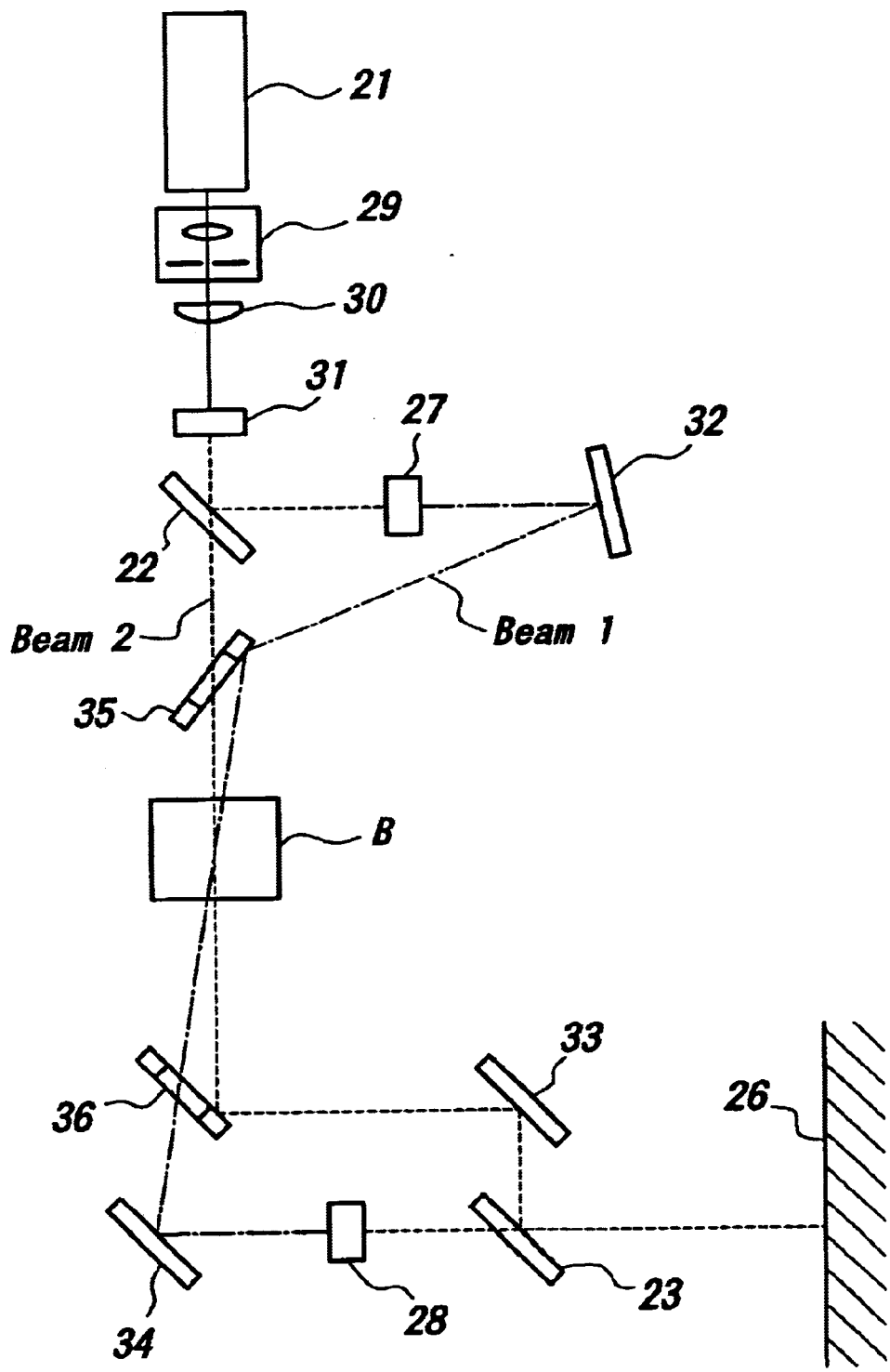
FIG. 2 is a structural view of another anisotropy analyzing apparatus according to the present invention, employed in another preferred embodiment of the anisotropy analyzing method of the present invention.

FIG. 2 is a structural view of another anisotropy analyzing apparatus according to the present invention, employed in another preferred embodiment of the anisotropy analyzing method of the present invention.

An anisotropy analyzing apparatus depicted in FIG. 2 has a laser source 21 to generate and oscillate a light beam to be used in the anisotropy analysis of a sample B, half mirrors 22, 23, and a screen 6 to project an interference pattern to analyze an anisotropy of the sample B.

Moreover, the anisotropy analyzing apparatus has half-wave plates 27 and 28 to rotate the light beam by 90 degrees, a spacial filter 29, a collimator lens 30, a polarizing plate 31, mirrors 32, 33, 34, and small mirrors 35 and 36 having openings at their centers.

A laser light beam from the laser source 21 passes through the spacial filter 29 and the collimator lens 30, and widened as mentioned above. Then, the light beam passes through the polarizing plate 31 to be converted into a plane wave. The plane wave is divided into two light beams through the half mirror 22.

One of the two divided light beams (beam 2) passes through the opening of the small mirror 35, and introduced into the sample B almost perpendicularly to the top surface of the sample B without the change of the traveling direction.

The other of the two divided light beams (beam 1) is transmitted to the half-wave plate 27, and its plane of polarization is rotated by 90 degrees through the half-wave plate 27. Then, the beam 1 is reflected at the mirror 32, and transmitted to the small mirror 35. The beam 1 is reflected at the edge of the small mirror 35, and introduced into the sample B so as to be crossed to the beam 2.

The beam 2 is transmitted to and reflected at the small mirror 36 after passing through the sample B, and is transmitted to the mirror 33 through the change of the traveling direction by 90 degrees. The beam 2 is transmitted at the mirror 33, and is transmitted to the half mirror 23 through the change of the traveling direction by 90 degrees.

The beam 1 passes through the opening of the small mirror 36 after passing through the sample B, and is transmitted to the mirror 34. Then, the beam 1 is transmitted to the half-wave plate 28 through the change of the traveling direction by almost 90 degrees. The plane of polarization of the beam 1 is rotated by 90 degrees so as to correspond to that of the beam 2 at the half-wave plate 28, and then, the beam 1 is transmitted to the half mirror 23.

The beams 1 and 2 having the same plane of polarization are superimposed at the half-wave mirror 23, and then, an interference pattern from the superimposed light beam is projected on the screen 26.

In this case, if the sample B has, at the crossing point of the beams 1 and 2 therein, an anisotropy such as a stress difference in the polarizing directions, the interference pattern is shifted from a normal interference pattern. Therefore, if the normal interference pattern is used as a standard interference pattern, the anisotropy of the sample B can be measured qualitatively from the degree of the interference pattern shift.

Moreover, if the parameters relating the interference pattern shift to the anisotropy of the sample B are known, the anisotropy can be measured quantitatively.

In this way, the two light beams are crossed at a given position inside the sample B.

Although the present invention was described in detail with reference to the above examples, this invention is not limited to the above disclosure and every kind of variation and modification may be made without departing from the scope of the present invention.

For example, in FIG. 1, although the plane of polarization of the beam 1 is rotated by 90 degrees so as to be orthogonal to that of the beam 2, the other way around will do. Moreover, although the plane of polarization of the beam 2 is rotated by 90 degrees so as to correspond to that of the beam 1 after the beam 2 passes through the sample A, the other way around will do.

Similarly, in FIG. 2, the plane of polarization of the beam 2 may be rotated by 90 degrees before the beam 2 is introduced into the sample B, instead of rotating the one of the beam 1 by 90 degrees. Moreover, the plane of polarization of the beam 2 may be rotated by 90 degrees so as to correspond to that of the beam 1, instead of rotating the one of the beam 1 so as to do ditto.

If a given wave plate is employed as substitute for the above half-wave plate, the plane of polarization of the beam 1 is rotated by given angles, and thus, the anisotropy of the sample in a give direction, corresponding to the polarizing directions of the beam 1, can be measured.

Moreover, a single plane polarized light beam may be introduced into the sample A or B directly, not through the half mirror 2, and divided into two light beams by a half mirror or the like after passing through the sample A or B. In this case, the divided light beams is superimposed by a half mirror or the like, and then, the anisotropy of the sample A or B can be measured from an interference pattern of the superimposed light beam.

As mentioned above, in the anisotropy analyzing method and the anisotropy analyzing apparatus according to the present invention, two light beams which are continuous in time and of which the planes of polarization are crossed each other are employed, so that the electrical synchronization for the two light beams is not required, different from the above conventional analyzing method. As a result, the total measuring system can be simplified. Then, expensive instruments are not needed, so that the cost of the total measuring system can be reduced. Moreover, since the two light beams are introduced into a sample, and irradiated to a given area of the sample at the same time, an anisotropy of the given area can be measured at the same time.

Moreover, according to the anisotropy analyzing method and the anisotropy analyzing apparatus of the present invention, the anisotropy of the sample can be measured without the density fluctuation due to the temperature change and the pressure change, and the anisotropy due to momentary structural change can be also measured.

What is claimed is:

1. A method for analyzing anisotropy of a sample comprising the steps of:
   preparing two light beams having the same wavelength of which the plane of polarization are crossed at a given angle,
   introducing the two light beams into a sample to be measured in anisotropy at the same time,
   rotating the plane of polarization of one of the two light beams by the given angle so as to correspond to that of the other of the two light beams, after passing the two light beams through the sample,
   superimposing the two light beams, and
   observing an interference pattern of the thus obtained superimposed light beam to analyze anisotropy of the sample.

2. The method as defined in claim 1, wherein the given angle is 90 degrees.

3. The method as defined in claim 1, comprising the step of superimposing the two light beams before introducing into the sample, whereby the thus obtained superimposed light beam is introduced into the sample.

4. The method as defined in claim 3, wherein the given angle is 90 degrees.

5. The method as defined in claim 1, wherein the two light beams are introduced into the sample so that their beam directions are crossed.

6. The method as defined in claim 5, wherein the given angle is 90 degrees.

7. An apparatus for analyzing anisotropy of a sample comprising:
   before a sample to be measured in anisotropy,
   a laser source to generate and oscillate a light beam to be used in anisotropy analysis,
   a light beam-dividing means to divide a light beam from the laser source into two light beams, and
   a first plane of polarization-rotating means to rotate the plane of polarization of one of the thus obtained two divided light beams by a given angle, after the sample to be measured in anisotropy, a second plane of polarization-rotating means to rotate the plane of polarization of the one or the other of the two divided light beams by the given angle so that their planes of polarization can correspond each other, a light beam-superimposing means to superimpose the two divided light beams, and a light beam-projecting means to project and observe an interference pattern of the thus obtained superimposed light beam.

8. The apparatus as defined in claim 7, wherein at least one of the first and the second plane of polarization-rotating means is composed of a half-wave plate.

9. The apparatus as defined in claim 7, wherein at least one of the light beam-dividing means and the light beam-superimposing means is composed of a half mirror.

10. The apparatus as defined in claim 7, further comprising:

before the sample to be measured in anisotropy, another light beam-superimposing means to superimpose the two divided light beams after the first plane of polarization-rotating means after the sample to be measured in anisotropy, a light beam-splitting means to split the superimposed light beam before the second plane of polarization-rotating means.

11. The apparatus as defined in claim 10, wherein at least one of the first and the second plane of polarization-rotating means is composed of a half-wave plate.

12. The apparatus as defined in claim 10, wherein at least one of the light beam-dividing means and the light beam-superimposing means is composed of a half mirror.

13. The apparatus as defined in claim 10, wherein the another light beam-superimposing means is composed of a half mirror.

14. The apparatus as defined in claim 10, wherein the light beam-splitting means is composed of a polarized light beam splitter.

* * * * *